US008808196B2

(12) United States Patent
Harada et al.

(10) Patent No.: US 8,808,196 B2
(45) Date of Patent: Aug. 19, 2014

(54) MEASURING DEVICE AND MEASURING METHOD FOR THRESHOLD OF FLICKER

(75) Inventors: Nobuyoshi Harada, Ikeda (JP); Sunao Iwaki, Ikeda (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 646 days.

(21) Appl. No.: 13/062,081

(22) PCT Filed: Aug. 27, 2009

(86) PCT No.: PCT/JP2009/064984
§ 371 (c)(1),
(2), (4) Date: Mar. 3, 2011

(87) PCT Pub. No.: WO2010/029858
PCT Pub. Date: Mar. 18, 2010

(65) Prior Publication Data
US 2011/0157261 A1 Jun. 30, 2011

(30) Foreign Application Priority Data

Sep. 10, 2008 (JP) .................................. 2008-231630
Feb. 26, 2009 (JP) .................................. 2009-043625

(51) Int. Cl.
*A61B 13/00* (2006.01)
*A61B 3/02* (2006.01)
*A61B 3/00* (2006.01)

(52) U.S. Cl.
USPC ............ 600/558; 351/222; 351/237; 351/239; 351/246

(58) Field of Classification Search
USPC ............ 600/558; 351/222, 237, 239, 243, 246
See application file for complete search history.

(56) References Cited

U.S. PATENT DOCUMENTS 4,940,323 A   7/1990 Downing
6,606,577 B1 * 8/2003 Fukuhara ..................... 702/127
(Continued)

FOREIGN PATENT DOCUMENTS

JP    10-192263    7/1998
JP    11-113888    4/1999
(Continued)

OTHER PUBLICATIONS

Supplementary European Search Report issued Nov. 9, 2011, in corresponding European Application No. 09 81 3005.7.
(Continued)

*Primary Examiner* — Devin Henson
(74) *Attorney, Agent, or Firm* — Wenderoth, Lind & Ponack, L.L.P.

(57) ABSTRACT

This invention relates to a flicker threshold measurement device including: an arithmetic processing unit 1; a display unit 8 with a fixed refresh rate; and an operation unit 9, wherein: the arithmetic processing unit 1 displays an image on the display unit 8 in an ON/OFF manner; the arithmetic processing unit 1 changes the display timing by monotonously increasing or decreasing the number of OFF periods per second; the arithmetic processing unit 1 monotonously increases or decreases at least one of: the number of OFF pixels in the image, the size of the image, and the contrast of the OFF pixels, during a period in which the display timing is not changed; each of the OFF periods is a reciprocal of the refresh rate; and the arithmetic processing unit 1 determines the number of OFF periods when a test subject 10 operates the operation unit 9 as he/she starts or stops perceiving flicker, as information corresponding to a flicker threshold. The present measurement device is capable of measuring a flicker threshold in a wide range of conditions, using a display apparatus with a fixed refresh rate (vertical synchronization frequency). Thereby, the present measurement device is useful for evaluating fatigue.

24 Claims, 9 Drawing Sheets

(56) References Cited

U.S. PATENT DOCUMENTS 8,029,138 B2 * 10/2011 Todd .......................... 351/222
2009/0270758 A1 10/2009 Eagleman et al.

FOREIGN PATENT DOCUMENTS

| JP | 2001-212117 | 8/2001 |
| JP | 2003-070773 | 3/2003 |
| WO | 2008/091399 | 7/2008 |

OTHER PUBLICATIONS

International Search Report issued Oct. 6, 2009 in International (PCT) Application No. PCT/JP2009/064984.

* cited by examiner

MEASURING DEVICE AND MEASURING METHOD FOR THRESHOLD OF FLICKER

TECHNICAL FIELD

The present invention relates to the measurement of a threshold at which a person starts recognizing flicker. The present invention particularly relates to a measuring device and a measuring method capable of measuring a flicker threshold using a CRT or a liquid crystal display which has a limited refresh rate. The measuring device and method are applicable to the evaluation of human mental fatigue (hereunder this may be simply referred to as "fatigue").

BACKGROUND ART

There is a known phenomenon in which a person becomes incapable of recognizing the flicker of a TV screens or the like that was visible when he/she was in a healthy condition. When light is alternately turned ON and OFF at a high speed, the human eye is incapable of perceiving the switching of the light, and instead perceives the light as being continuously ON (in the case of a display device, they perceive the image as being constantly displayed). When the frequency for turning the light ON and OFF is gradually decreased, the flicker of the light becomes visible at a certain frequency. This frequency is called the flicker value (Critical flicker fusion rate: CFF). It is known that although the flicker value is relatively high for persons who are in a generally healthy condition, the value decreases with the increase of fatigue and, in particular, mental fatigue. Using this phenomenon, Simon & Enzer et al. (1941) proposed a flicker value examination method more than about 65 years ago. This method evaluates the degree of mental fatigue based on the decrease in the flicker value. Since then, the flicker value has been used as an index of mental fatigue or level of arousal in the field of ergonomics and occupational health.

This flicker value examination method is well recognized as combining numerous excellent properties, such as (1) the confirmation of (constant) changes in the measurement value with the application of a continuous fatigue load, (2) a constant correlation between changes in the measurement value and changes in the condition of activity (e.g., working efficiency), (3) a small fluctuation among measured values, and (4) a close relationship with the activity level of the cerebral cortex. Despite such advantages, the flicker value examination method did not become widely used due to the huge size of its measurement device.

The flicker value measurement method is disclosed, for example, in Patent Literatures 1 and 2 below. Patent Literature 1 discloses a flicker sensitivity distribution measurement device comprising a display for emitting a blinking light target. This apparatus uses blinking frequencies of 5 Hz, 10 Hz, 20 Hz, and 30 Hz.

Patent Literature 2 discloses a system comprising a blinking light emission apparatus and a computer terminal. In the system, the blinking light emission apparatus that is controlled by a computer via a communication cable displays flicker stimulation; and the computer records the test subject's button-pressing operations, each of which indicates the perception of flicker. The recorded data is then compared with previously measured data to evaluate the degree of fatigue.

Further, it is reported that the flicker value is proportional to the modulation (change) amount of the light stimulation. For example, it is reported that the flicker value is greater in long-duration flicker stimulation than in short-duration flicker stimulation, and that the flicker value is greater in high-luminance flicker stimulation than in low-luminance flicker stimulation. Moreover, it is also reported that the flicker value changes depending on the size or color of the stimulation object.

CITATION LIST

Patent Literature

PTL 1: Japanese Unexamined Patent Publication No. 1999-113888
PTL 2: Japanese Unexamined Patent Publication No. 2003-70773

SUMMARY OF INVENTION

Technical Problem

As described above, the flicker value examination method did not become widely used due to the huge size of its measurement device. Further, even today, the flicker value examination requires that the light-blinking cycle be controlled in units of at least 1 Hz; therefore, the flicker value examination must use a special apparatus using LEDs or the like that is capable of strictly controlling the ON/OFF switching. Accordingly, the examination is expensive and its operation is complicated. This is one of the main factors hindering the wide use of the flicker value examination method in spite of its ability to provide stable measurement of fatigue level.

In recent years, with advances in electronics and computer technology, devices with image-displaying functions, such as computers, mobile phones, etc., are in wide use. In computers and mobile phones, visual information is generally displayed while refreshing the display at a fixed rate (a refresh rate). The refresh rate refers to the cycles per second (Hz) of refreshing the displayed image. Therefore, these devices may be used to display blinking lights. However, their refresh rates are limited. For example, the refresh rate of a computer's liquid crystal display is generally about 60 Hz, so when the blinking light display is performed with equal ON/OFF periods, as in the conventional flicker value measurement, the ON/OFF frequency is limited to 30 Hz, 15 Hz, 7.5 Hz, 3.25 Hz, etc. The flicker value examination cannot be performed with this limitation.

Patent Literature 1 discloses displaying a blinking target using a display with a blinking frequency of 5 Hz, 10 Hz, 20 Hz, and 30 Hz; however, the invention of Patent Literature 1 has no description of the refresh rate of the display. Since all of those disclosed frequencies cannot be performed with a fixed refresh rate, it is likely that the refresh rate is changed in Patent Literature 1.

In Patent Literature 2, the computer is used only to control the blinking conditions of a special blinking light display device. The display unit of the computer is not used as a blinking light display.

In view of the above problems, an object of the present invention is to provide a measurement device and a measurement method that are capable of measuring flicker threshold in a wide range of conditions using a general display device that refreshes the display at a specific refresh rate, and that can be used for evaluating human mental fatigue.

Solution to Problem

The inventors of the present invention found that, by measuring the threshold at which the test subject starts recognizing flicker as a modulation (change) amount of the stimulation target, instead of measuring it simply as a frequency, it becomes possible to evaluate human fatigue using a display device that has a limited light blinking frequency due to a fixed refresh rate. By thus detecting changes in the modulation amount of the target, the device becomes capable of measuring human mental fatigue. With this finding, the inventors completed the present invention.

Specifically, a first flicker threshold measurement device according to the present invention comprises:

an arithmetic processing unit;

a display unit that refreshes an image at a specific refresh rate; and an operation unit, wherein:

the arithmetic processing unit displays an image on the display unit in an ON/OFF manner at a predetermined timing;

the arithmetic processing unit changes the timing with time by monotonously increasing or decreasing a number of OFF periods, during which an image is not displayed, per second;

the OFF period is a reciprocal of the refresh rate; and the arithmetic processing unit determines the number of OFF periods at a time where a test subject operates the operation unit as he/she starts or stops perceiving flicker, as information corresponding to a flicker threshold.

Further, a second flicker threshold measurement device according to the present invention comprises:

an arithmetic processing unit;

a display unit that refreshes an image at a specific refresh rate; and an operation unit, wherein:

the arithmetic processing unit displays an image on the display unit in an ON/OFF manner at a predetermined timing;

the arithmetic processing unit monotonously increases or decreases at least one of: number of OFF pixels in the image, size of the image, and contrast of the OFF pixels, with time; and the arithmetic processing unit determines the number of OFF pixels at a time when a test subject operates the operation unit as he/she starts or stops perceiving flicker, as information corresponding to a flicker threshold.

Further, a third flicker threshold measurement device according to the present invention comprises:

an arithmetic processing unit;

a display unit that refreshes an image at a specific refresh rate; and an operation unit, wherein:

the arithmetic processing unit displays an image on the display unit in an ON/OFF manner at a predetermined timing;

the arithmetic processing unit changes a color of the image with time; and the arithmetic processing unit determines a number of OFF pixels at a time when a test subject operates the operation unit as he/she starts or stops perceiving flicker, as information corresponding to a flicker threshold.

Further, a fourth threshold measurement device according to the present invention is arranged such that, based on the first threshold measurement device, the arithmetic processing unit monotonously increases or decreases with time at least one of: number of OFF pixels in the image, size of the image, and contrast of the OFF pixels, during a period in which the timing is not changed.

Further, a fifth flicker threshold measurement device according to the present invention is arranged such that, based on the first, second or fourth threshold measurement device, the arithmetic processing unit changes a color of the image with time, during a period in which the timing is not changed.

Further, a first process for measuring a flicker threshold according to the present invention uses an apparatus comprising:

an operation unit; and a display unit that refreshes an image at a specific refresh rate, and the process comprises the steps of:

1) displaying an image on the display unit in an ON/OFF manner at a predetermined timing;

2) changing the timing with time by monotonously increasing or decreasing a number of OFF periods, during which an image is not displayed, per second; and 3) determining the number of OFF periods at a time when a test subject operates the operation unit as he/she starts or stops perceiving flicker, as information corresponding to a flicker threshold, wherein:

the OFF period is a reciprocal of the refresh rate.

Further, a second process for measuring a flicker threshold according to the present invention uses an apparatus comprising:

an operation unit; and a display unit that refreshes an image at a specific refresh rate, and the process comprises the steps of:

1) displaying an image on the display unit in an ON/OFF manner at a predetermined timing;

2) monotonously increasing or decreasing at least one of: number of OFF pixels in the image, size of the image, and contrast of the OFF pixels, with time; and 3) determining the number of OFF pixels at a time when a test subject operates the operation unit as he/she starts or stops perceiving flicker, as information corresponding to a flicker threshold.

Further, a third process for measuring a flicker threshold according to the present invention uses an apparatus comprising:

an operation unit; and a display unit that refreshes an image at a specific refresh rate, and the process comprises the steps of:

1) displaying an image on the display unit in an ON/OFF manner at a predetermined timing;

2) changing a color of the image with time; and 3) determining a number of OFF pixels at a time when a test subject operates the operation unit as he/she starts or stops perceiving flicker, as information corresponding to a flicker threshold.

Further, a fourth process for measuring a flicker threshold according to the present invention causes the device to further carry out the step of, based on the first process, 4) monotonously increasing or decreasing with time at least one of: number of OFF pixels in the image, size of the image, and contrast of the OFF pixels, during a period in which the timing is not changed.

Further, a fifth process for measuring a flicker threshold according to the present invention causes the device to further carry out the step of, based on the first, second or fourth process, 5) changing a color of the image with time, during a period in which the timing is not changed.

Further, a sixth threshold measurement device according to the present invention comprises:

an arithmetic processing unit;

a blinking unit capable of being turned ON and OFF at a changeable blinking frequency; and an operation unit, wherein:

the arithmetic processing unit specifies a first blinking cycle and a second blinking cycle of the blinking unit in units of milliseconds;

the arithmetic processing unit turns ON and OFF the blinking unit by monotonously increasing or decreasing with time a number of OFF periods to be changed into ON periods among continuous n+1 OFF periods, where n is a number of third frequencies that can be set between a first frequency corresponding to the first blinking cycle and a second frequency corresponding to the second blinking cycle;

the OFF period is ½ of the first blinking cycle or the second blinking cycle; and the arithmetic processing unit determines the number of OFF periods changed to ON periods when a test subject operates the operation unit as he/she starts or stops perceiving flicker, as information corresponding to a flicker threshold.

Further, a sixth process for measuring a flicker threshold according to the present invention uses an apparatus comprising:

an operation unit; and a blinking unit capable of being turned ON and OFF at a changeable blinking frequency;

and the process comprises the steps of:

1) specifying a first blinking cycle and a second blinking cycle of the blinking unit in units of milliseconds;

2) turning ON and OFF the blinking unit by monotonously increasing or decreasing with time a number of OFF periods to be changed into ON periods among continuous n+1 OFF periods, where n is a number of third frequencies that can be set between a first frequency corresponding to the first blinking cycle and a second frequency corresponding to the second blinking cycle; and 3) determining the number of OFF periods changed to ON periods when a test subject operates the operation unit as he/she starts or stops perceiving flicker, as information corresponding to a flicker threshold;

wherein:

the OFF period is ½ of the first blinking cycle or the second blinking cycle.

Advantageous Effects of Invention

The present invention is capable of creating stimulation of a wider dynamic range and presenting the stimulation to a test subject by using widely used computers and mobile devices with limited refresh rates, thereby making it possible to measure flicker threshold in a manner similar to the conventional standard flicker value measurement method.

Therefore, by using the present invention to obtain the flicker threshold of a test subject while the test subject is free from fatigue, and then to again obtain a flicker threshold for the same test subject and compare the two thresholds, it can be determined whether or not the test subject is experiencing fatigue.

Moreover, this method allows test subjects to measure the flicker threshold and evaluate fatigue by using, for example, their own computers or mobile phones. Thereby, the present invention is useful for self management purposes.

DESCRIPTION OF EMBODIMENTS

Most CRTs or liquid crystal displays that serve as a display device for computers or mobile phones refresh their displays at a fixed refresh rate (the cycles per second at which the display is refreshed). Computers are capable of changing the refresh rate within a limited range; however, once the refresh rate is determined, the value is continuously used until a different value is set. Generally, for example, the flicker frequency that appears by simply turning the light on and off for a screen in which the refresh rate is 60 Hz is half of the refresh rate value, i.e., 30 Hz. Generally, when measurement is performed using LED light or the like with a high luminance, flicker stimulation of 30 Hz is easily perceived by a person in a healthy condition. On the other hand, it is known that flicker can become unperceivable due to changes in the contrast, frequency (number of OFF pixels), size, etc., of the pixels in the image (hereinafter also referred to as a stimulation target) being turned ON and OFF on the display device. It is also known that the flicker value has a characteristic such that it is proportional to the modulation amount of the stimulation target.

Therefore, the present invention proposes, as a flicker threshold measurement method, a method (a temporal coding method) that takes the temporal modulation amount of a stimulation target as temporal coding, and changes the frequency (the ON/OFF frequency) of altering the light per unit time; a method (a spatial coding method) that takes the spatial modulation amount of the stimulation target as spatial coding, and changes (the frequency or) the number of pixels that alter the light of the stimulation target, the contrast of the pixels, the size of the stimulation target, or the color of the stimulation target; and a method (a temporal-spatial coding method) that combines the temporal coding method and the spatial coding method.

Figure 1:
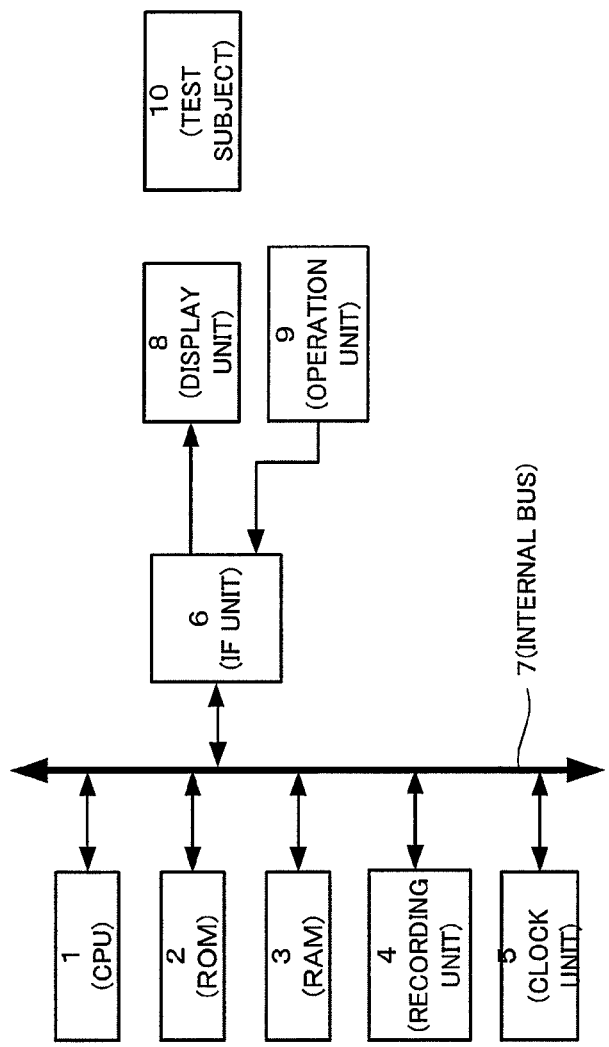
[FIG. 1] A block diagram showing a flicker threshold measurement device, according to an embodiment of the present invention.

An embodiment of the present invention is described below in reference to the attached drawings. FIG. 1 is a block diagram showing a flicker threshold measurement device, according to an embodiment of the present invention.

The measurement device of the present invention comprises an arithmetic processing unit (hereinafter referred to as a CPU) 1 for controlling the entire apparatus; a nonvolatile read-only memory (hereinafter referred to as a ROM) 2 storing a program, etc.; a volatile rewritable memory (hereinafter referred to as a RAM) 3 for temporarily storing data; a nonvolatile rewritable recording unit 4 for continuously storing data; a clock unit 5; an interface unit (hereinafter referred to as an IF unit) 6 for interfacing with external apparatuses; an internal bus 7 for exchanging data (including control information) between units; a display unit 8; and an operation unit 9. A known computer or mobile device (mobile phone, PHS, PDA, etc.), for example, can be used for the present measurement device.

The operation unit 9 includes operating means such as keys or pads. The display unit 8 includes a display screen (such as a liquid crystal display) and a drive unit for driving the display. The clock unit 5 is a means for outputting current time information using an internal clock such as a timer.

The following briefly describes the operation of the present measurement device. According to previously specified conditions, the CPU 1 generates the image data to be displayed on the display unit 8 at a predetermined timing, and sends the data to the display unit 8 via the IF unit 6. The signal supplied to the display unit 8 is digital data or an analog video signal converted by the IF unit. The display unit 8 displays the received image data to a test subject 10 at a predetermined refresh rate. The CPU 1 generates an image that changes according to previously specified conditions. The state of the image displayed on the display unit 8 thereby changes. The test subject 10 observes the image displayed on the display unit 8, and operates the operation unit 9 when he/she recognizes the appearance or disappearance of flicker. This operation information is sent to the CPU 1 via the IF unit 6, and is recorded in the RAM 3 or the recording unit 4.

As described, the state of the image displayed toward the test subject is changed, and the perception of flicker by the test subject is thereby evaluated. Unlike the conventional method of gradually increasing or decreasing the frequency and recoding the frequency at which the test subject starts to perceive the flicker, the present invention changes the size, contrast, etc., of the displayed image at a limited range of frequency, and records the condition in which the test subject starts to perceive the flicker, or the condition in which the test subject stops perceiving the flicker, as the flicker threshold.

Figure 2:
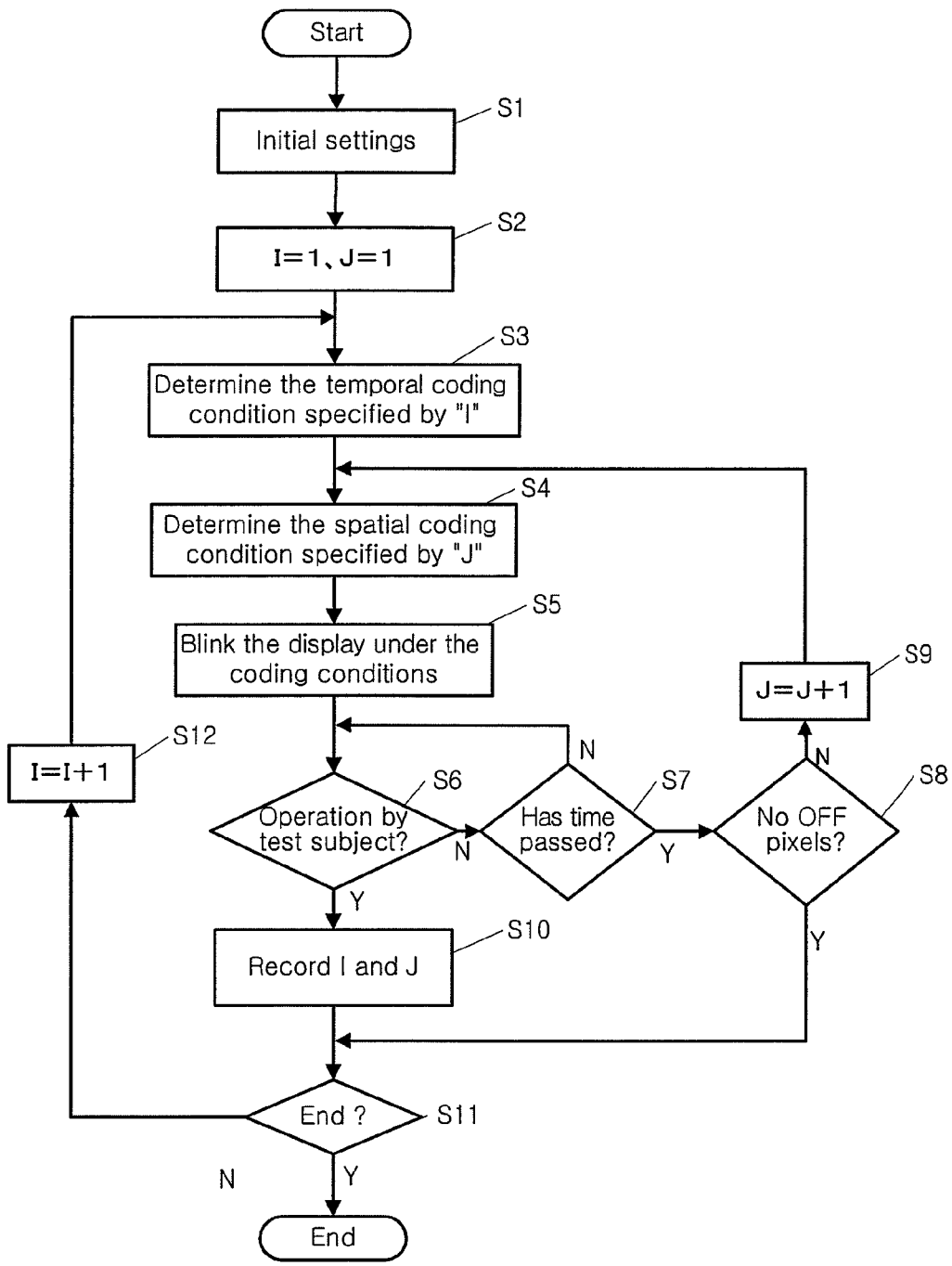
[FIG. 2] A flow chart showing the operation of a flicker threshold measurement device, according to an embodiment of the present invention.

The present measurement device is specifically explained below. FIG. 2 is a flow chart showing the operation of a flicker threshold measurement device according to the present embodiment. The following steps are carried out by the CPU 1, unless otherwise specified. As required, the CPU 1 reads out all of the necessary data items (including programs) from the ROM 2 or the recording unit 4, and develops the data in the RAM 3 to carry out data processing using a predetermined working area of the RAM 3. Then, the CPU 1 records temporary results or final processing results in the recording unit 4 as required.

First, a menu is displayed on the display unit 8 to allow the test subject 10 to select whether or not to carry out the measurement. When the test subject 10 operates the operating unit 9 to select fatigue measurement, the following steps are carried out.

In Step S1, the initial settings are made. More specifically, the frequency for turning on and off an image and information regarding changes in the frequency (hereinafter referred to as the temporal coding condition); the size (shape) of the image and information regarding changes in the size (shape) (hereinafter referred to as the spatial coding condition); and a time Δ for turning on and off an image in one type of temporal coding condition and spatial coding condition, are read out from the recording unit 4. Further, a time coding number N and a maximum pixel number P of the image to be displayed are also read out from the recording unit 4.

Figure 3:
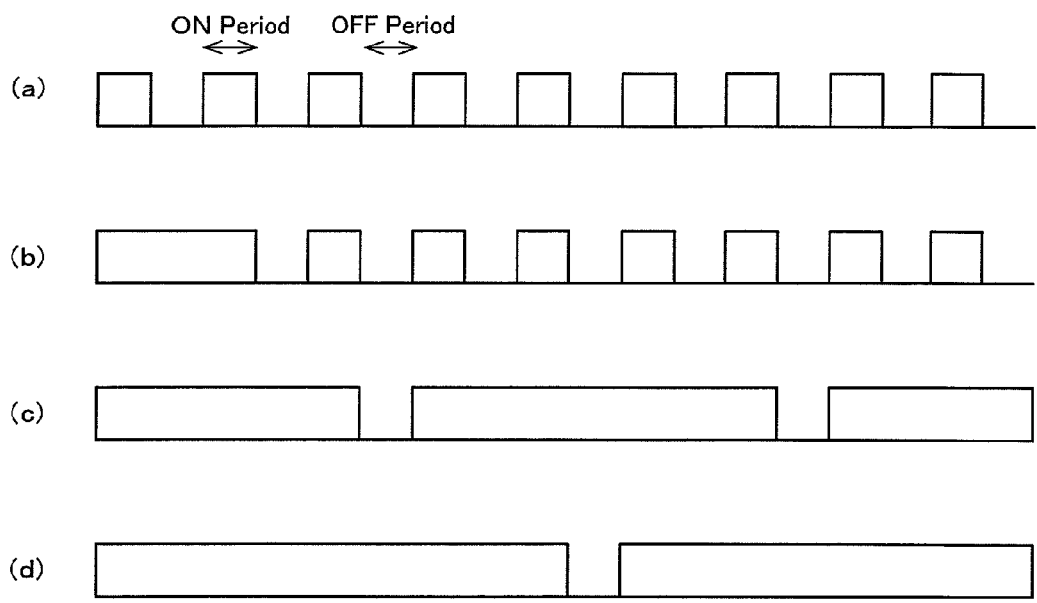
[FIG. 3] A diagram showing an example of temporal coding conditions.
Figure 4:
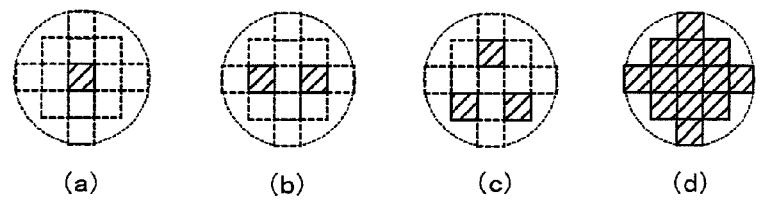
[FIG. 4] A diagram showing an example of spatial coding conditions.

FIGS. 3 and 4 show examples of the temporal coding condition and spatial coding condition, respectively.

As shown in FIG. 3, the temporal coding condition is information regarding the timing for turning on and off the entire image. FIG. 3 shows conditions for turning on and off an image. In the figure, the refresh rate of the display unit is set to 60 Hz (that is, the time for turning on and off an image is about 16.6 ms), and the horizontal axis and the vertical axis represent time and luminance as the ON/OFF state of an image, respectively. In FIG. 3(*a*), the image is turned off 30 times per second. More specifically, the ON/OFF frequency is 30 Hz, which is the maximum value for a refresh rate of 60 Hz. FIG. 3(*b*) shows the next state after FIG. 3(*a*), in which the image is turned off 29 times per second. In FIG. 3(*b*), the leftmost OFF period is changed to an ON period; however, it is also possible to change a different OFF period to an ON period. The number of OFF periods is sequentially decreased to the final state shown in FIG. 3(*d*) in which the image is turned off only once per second.

On the other hand, as shown in FIG. 4, the spatial coding condition is information regarding pixels that constitute an image. FIG. 4 shows an image comprising 13 pixels (the broken line denotes a circumscribed circle). Each pixel is schematically shown as a square. The shaded pixels are in an ON state (hereinafter referred to as ON pixels), while the white pixels are in an OFF state (hereinafter referred to as OFF pixels). Here, all of the luminance values of the ON pixels are the same and all of the luminance values of the OFF pixels are also the same (data=0). As time passes, the displayed image changes from the state of (a) through (d). In (a), 12 pixels are OFF (only one pixel is ON). 4(b) shows an image after (a), in which 11 pixels are OFF (2 pixels are ON). In (c), 10 pixels are OFF (3 pixel are ON). In this manner, the number of OFF pixels decreases one by one (the number of ON pixels increases one by one); finally, all 13 pixels are ON, as shown in FIG. 4(*d*).

As described, the temporal coding condition and the spatial coding condition are information items used to allow the CPU 1 to change the displayed image on the display unit 8, for example, as in FIGS. 3 and 4.

In Step S2, an initial value 1 is set in the counters I and J that are used in the following repeating processes.

In Step S3, the temporal coding condition is determined according to the condition I=1. In Step S4, the spatial coding condition is determined according to the condition J=1. More specifically, coding conditions corresponding to I and J are read out from temporal and spatial coding conditions previously stored in the recording unit 4.

In Step S5, an image is generated according to the conditions determined in Steps S3 and S4, and the image is displayed on the display unit 8. For example, assuming that FIG. 3(*a*) corresponds to the temporal coding condition I=1 and FIG. 4(*a*) corresponds to the spatial coding condition J=1, the measurement under a condition where I=1 and J=1 is carried out as follows. First, the image shown in FIG. 4(*a*) is generated and the image is displayed on the display unit 8. The image display is maintained for the ON period shown in FIG. 3(*a*). When the OFF period begins, the display of the entire image is stopped. Immediately before starting the ON/OFF image display, time data is acquired from the clock unit 5. This time data is referred to as start time T.

In Step S6, a judgment is made as to whether the test subject 10 operates the operation unit 9 (for example, whether a key is pressed). For example, in Step S5, a text message that reads "Press the key when flickering begins." or the like is displayed on the display unit 8 before the ON/OFF display of the image begins. If the test subject 10 presses a key as he/she perceives the flicker of the image displayed on the display unit 8, the sequence goes to Step S10. If the key is not pressed by the test subject 10, the sequence goes to Step S7.

In Step S7, the current time t is acquired from the clock unit 5 to be compared with the start time T. If the difference (t−T) is smaller than the time Δ (t−T<Δ), the sequence goes back to Step S6. If the difference (t−T) is equal to or greater than the time Δ (t−T≥Δ), the sequence goes to Step S8. As such, when key-pressing by the test subject 10 is not detected, the ON/OFF display is continued for the time Δ.

In Step S8, a judgment is made as to whether all of the pixels constituting the image are in the ON state, i.e., whether there are no OFF pixels. If there are any OFF pixels in the image, the sequence goes to Step S9 and 1 is added to the value J. Then, the sequence goes to Step S4. The judgment in S8 is carried out, for example, by subtracting the current J value from the maximum pixel number P read out in Step S1, and determining whether the value (P−J) is 0.

When Steps S4 to S6 are carried out under the condition of J=2, in Step S4, a spatial coding condition corresponding to J=2 (for example, the condition shown in FIG. 4(b)) is set, and in Step S5, the ON/OFF display of the image is carried out under a temporal coding condition corresponding to I=1 (the condition shown in FIG. 3(a)) and a spatial coding condition corresponding to J=2 (the condition shown in FIG. 4(b)) in the same manner as in the condition where I=1 and J=1. As described above, the ON/OFF display of the image is continued until the test subject 10 operates the operation unit 9, or time has elapsed.

The same sequence is performed when Steps S4 to S6 are carried out under the condition of J≥3. In Step S4, a spatial coding condition corresponding to J (for example, when J=3, the condition shown in FIG. 4(c)) is set, and in Step S5, the ON/OFF display of the image is carried out under a temporal coding condition corresponding to I=1 (the condition shown in FIG. 3(a)) and a spatial coding condition corresponding to J (when J=3, the condition shown in FIG. 4(c)).

As described, Steps S4 to S9 are repeated until the test subject 10 operates the operation unit 9, performing the ON/OFF display of the image under a temporal coding condition corresponding to an I value (I=1) while decreasing the frequency of the OFF pixels (the number of OFF pixels in the image).

In Step S10, as described above, the values I and J at the time where a key is pressed are associated with each other and are stored in the recording unit 4.

Next, in Step S11, a judgment is made as to whether or not to finish the sequence, in other words, as to whether there are any unused temporal coding conditions left. The judgment is made, for example, by subtracting the current I value from the temporal coding number N read out in Step S1 and determining whether the value (N−I) is 0. If it is determined not to finish the sequence, the sequence goes to Step S12 and 1 is added to the value I. Then, the sequence goes to Step S3.

When Steps S3 to S10 are carried out under the condition of I=2, in Step S3, a temporal coding condition corresponding to I=2 (for example, the condition shown in FIG. 3(b)) is set, and in Steps S4 to S10, the ON/OFF display of the image is carried out under a spatial coding condition corresponding to J (the condition shown in FIG. 4(a) to FIG. 4(d)), in the same manner as in the condition where I=1. More specifically, the images shown in FIG. 4(a) to FIG. 4(d) are sequentially generated, and the images are displayed on the display unit under a temporal coding condition I=2 (for example, the condition shown in FIG. 3(b)).

The same sequence is carried out when Steps S3 to S10 are carried out under the condition of I≥3. In the case where I=3, for example, the images of FIG. 4(a) to FIG. 4(d) are sequentially generated under the temporal coding condition of FIG. 3(c), thereby performing the ON/OFF display of the images.

As described, the above Steps S1 to S11 enable an image to be displayed for a test subject in a manner such that the image is turned ON and OFF under a predetermined temporal coding condition while changing the spatial coding condition, i.e., while changing the state of the image to be displayed. Therefore, by allowing the test subject to operate the operation unit in response to perception of flicker, it is possible to determine and record the values I and J corresponding to the temporal coding condition and spatial coding condition at the time, as information indicating a flicker threshold.

As described above, a flicker threshold is measured and recorded when the test subject is free from fatigue. Thereafter, by measuring the flicker threshold again for the same test subject in the same manner and comparing the obtained threshold with the value obtained when the test subject was free from fatigue, it is possible to determine whether the test subject is experiencing fatigue. More specifically, since the flicker threshold changes when a person is experiencing fatigue, it is possible to determine whether the test subject is experiencing fatigue by evaluating the degree of change in the flicker threshold based on the flicker threshold obtained when the test subject was free from fatigue. For example, if the flicker threshold is changed by a certain value or greater, it is determined that the test subject is experiencing fatigue. Here, the flicker threshold is generally multidimensional data, as it is specified by the temporal coding condition and spatial coding condition. Therefore, it is possible to find the difference in the spatial coding condition for each of the corresponding temporal coding conditions, thereby finding the average, maximum, intermediate values, etc., of the obtained values. It is also possible to plot the multidimensional flicker thresholds on a graph to evaluate the degree of change. Further, other known methods for evaluating the degree of change in the flicker threshold may also be used.

In addition, the flicker threshold may be measured using only one of the coding conditions, i.e., only the temporal coding condition or only the spatial coding condition. However, in this case, the dynamic range and the number of steps of the measurement are limited. In contrast, as described above, by simultaneously changing the temporal coding condition and spatial coding condition, there is no such restriction and the image display can be performed with a stimulation image having a wider dynamic range equivalent to the conventional standard flicker value measurement method (which enables the display of stimulation in a wide frequency range). More specifically, if the compatibility with the standard flicker value measurement method is to be considered, it is preferable to measure the flicker threshold by simultaneously changing both the temporal coding condition and spatial coding condition.

The present invention is not limited to the above embodiment, but may be altered by changing the structure and the process of the apparatus, for example, as follows.

The present invention is not limited to the above case in which the refresh rate is 60 Hz and the maximum number of displayed pixels is 13. The ON period and OFF period are equal values (1/f (seconds)) determined by the refresh rate f (Hz). The maximum number of OFF period per second is f/2 (times). Therefore, a decrease in the number of OFF periods starts from f/2 (times).

The value from which the number of OFF periods is reduced and the reduction value of the OFF periods per reduction may be arbitrarily determined. Therefore, instead of starting the reduction from f/2 (corresponding to 30 Hz in the above example), it is possible to start it from a slightly smaller value (natural number). Moreover, the reduction value is not limited to 1, but may be 2, 3 or a larger number (natural number). It is also possible to change the value directly to a predetermined value (for example, 30, 15, 4, 1, etc.).

Moreover, the shape and size (number of pixels) of the image to be displayed may be arbitrarily determined. For example, even when the same number of OFF pixels is used, the positions of the OFF pixels may be arbitrarily determined.

Although the luminance values of the ON pixels and OFF pixels were the same, respectively, for each case in the above example, the flicker threshold may be measured in the above manner by changing the luminance value of the OFF pixels (contrast) with time. It is also possible to change the color of the image to be displayed. These changes are also included in the spatial coding condition. The changes are more specifically described in the later-described Examples (in the Examples, a change in the luminance value of the OFF pixels is expressed as a change in contrast). As for the order of processing, for example, in the case of changing the contrast in the flow chart shown in FIG. 2, a new repetition count K is created, and a counter K loop (a process for changing contrast) is incorporated into the counter J loop (Steps S4 to S9). It is also possible to perform a process for changing the contrast in Step S4 without changing the size of the image. It is also possible to change the color in the same way.

Furthermore, although the temporal coding condition is changed in the above example so that the number of OFF periods of the image monotonously decreases with time, the present invention is not limited to this. For example, it is also possible to change the temporal coding condition so that the number of OFF periods of the image monotonously increases with time. Also, although the spatial coding condition is changed so that the number of OFF periods decreases with time in the above case, the present invention is not limited to this. For example, it is also possible to change the spatial coding condition so that the number of OFF periods increases from 1. In these cases, when the measurement is started with the test subject perceiving flicker, the temporal and spatial coding condition at which the test subject stops perceiving flicker can be obtained.

Furthermore, although the spatial coding condition is changed for each temporal coding condition in the above example, the present invention is not limited to this. For example, it is also possible to display the image by changing the temporal coding condition for each spatial coding condition.

Moreover, in the above example, the repetition counters I and J are recorded as information regarding flicker threshold; however, a temporal or spatial coding condition themselves at which the test subject starts perceiving a flicker, or information for specifying these conditions, may be used.

Moreover, instead of generating images by the CPU 1 in real time, it is possible to suitably read out image data which was previously generated and recorded in the recording unit.

It is also possible to measure the flicker threshold by displaying a stimulation image while changing the image by the backlight of a liquid crystal display on a mobile phone or the like. Generally, the blinking cycle of a backlight can be specified in milliseconds (ms). Therefore, it is possible to display flicker at a maximum frequency of about 1 kHz. When a backlight is used for flicker threshold measurement, the backlight must have a frequency band of several Hz to several tens of Hz; however, in this frequency band, the flicker of the backlight cannot be changed at 1-Hz intervals, thereby causing frequency jumping. Therefore, to measure the flicker threshold using a backlight, it is preferable to apply the temporal coding method of the present invention. More specifically, it is preferable to cause the arithmetic processing unit of a mobile phone to blink the backlight using a memory or the like under the later-described temporal coding condition. When this is done, the displayed pattern in the liquid crystal display is fixed, i.e., it does not change with time. The displayed pattern may have an arbitrary shape, for example, white (but not necessarily at the maximum luminance) may be displayed over the entire liquid crystal display, or in a predetermined area near the center of the display.

Table 1 shows some cases of frequency jumping and temporal coding conditions for compensating the frequency jumping.

TABLE 1

| Specified cycle (ms) | ON period (ms) | Actual frequency (Hz) | Target frequency (Hz) | Intermediate display method |
|---|---|---|---|---|
| 16 | 8 | 62.50 | 62 | 1/7, 2/7, 3/7, 4/7, 5/7, 6/7 |
| 18 | 9 | 55.55 | 55 | 1/5, 2/5, 3/5, 4/5 |
| 20 | 10 | 50.00 | 50 | 1/5, 2/5, 3/5, 4/5 |
| 22 | 11 | 45.45 | 45 | 1/4, 2/4, 3/4 |
| 24 | 12 | 41.66 | 41 | 1/3, 2/3 |
| 26 | 13 | 38.46 | 38 | 1/3, 2/3 |
| 28 | 14 | 35.71 | 35 | 1/3, 2/3 |
| 30 | 15 | 33.33 | 33 | 1/3, 2/3 |
| 32 | 16 | 31.25 | 31 | 1/2 |
| 34 | 17 | 29.41 | 29 | 1/2 |
| 36 | 18 | 27.77 | 27 | 1/2 |

"Specified cycle" refers to a specified cycle to blink the backlight. In the examples of Table 1, the cycles are specified as intervals of 2 ms. "ON period" refers to a time automatically determined according to a specified cycle to turn ON the backlight. "ON period" also refers to half the value of a "specified cycle". Accordingly, an "OFF period" in which the backlight is turned OFF is the same value as the "ON period". "Actual frequency" refers to the blinking frequency of the backlight that is determined by the specified cycle. "Target frequency" is an integer close to the actual frequency, and corresponds to the values that are set in 1-Hz intervals in the conventional method.

As such, since the specified cycle is usually an integer value, the usable blinking frequency (actual frequency) of the backlight cannot be changed at 1 Hz intervals. For example, the first line of Table 1 shows that, when 16 ms is set as the specified cycle, the actual frequency becomes 62.50 Hz, which can be used as a target frequency of 62 Hz. The second line of Table 1 shows that, when 18 ms is set as the specified cycle, the actual frequency becomes 55.55 Hz, which can be used as a target frequency of 55 Hz. Accordingly, there is about 7 Hz difference between the actual frequencies 62.50 Hz and 55.55 Hz (between the target frequencies 62 Hz and 55 Hz). Therefore, the target frequencies in between, i.e., the target frequencies 61, 60, 59, 58, 57, and 56 Hz, cannot be performed.

These frequencies can be compensated by using the temporal coding method of the present invention. More specifically, the "Intermediate display method" column in Table 1 shows temporal coding conditions corresponding to those frequencies that cannot be performed in the above manner. For example, the rightmost cell of the first row shows temporal coding conditions corresponding to the six frequencies (61, 60, 59, 58, 57, and 56 Hz) required between the target frequency (62 Hz) in the first row and the target frequency (55 Hz) in the second row. More specifically, this cell indicates measurements made with temporal coding conditions 1/7, 2/7, 3/7, 4/7, 5/7 and 6/7 using a specified cycle of 16 ms (ON period=8 ms). The rightmost cell of second and later rows shows a similar measurement. The rightmost cell in the bottom row of Table 1 shows a temporal coding condition corresponding to a frequency (specifically, 26 Hz) between the target frequency 27 Hz and the next target frequency 25 Hz (omitted).

The temporal coding condition shown in Table 1 is the same as that explained above in reference to FIG. 3. More specifically, the denominators represent the number of sets of ON/OFF periods considered as one group among the consecutive ON/OFF periods, and the numerators represent the number of sets of ON/OFF periods wherein the duration of each of the ON and OFF periods is increased by one unit of time among the ON/OFF periods considered as one group. For example, the temporal coding condition 1/7 refers to a condition in which the duration of only one ON/OFF period among seven consecutive sets of ON/OFF periods is prolonged in such a manner that each of the ON and OFF periods is increased by one unit of time. That is, only one out of the seven sets of ON/OFF periods is changed in such a manner that the backlight is blinked at a blinking frequency that is longer by one unit of time than the blinking cycle indicated by the specified frequency. Similarly, the temporal coding condition 4/5 refers to a condition in which the duration of four sets of ON/OFF periods among five consecutive sets of ON/OFF periods is prolonged in such a manner that each of the ON and OFF periods in all four sets of ON/OFF periods is increased by one unit of time. That is, the backlight is blinked under the condition such that each of the ON and OFF periods in four of the five sets of ON/OFF periods is prolonged by one unit of time.

As described, when the interval between adjacent frequencies among the frequencies attainable by a backlight is 1.5 Hz or greater, the temporal coding method of the present invention enables the measurement of flicker thresholds substantially corresponding to the blinking frequencies that cannot be attained. Further, the temporal coding method of the present invention is, of course, applicable when the "specified cycle" is set to an interval other than 2 ms, for example, 1 ms.

Further, this is not limited to a backlight. An LED and other blinking stimulation display means may also have blinking frequencies that cannot be attained if the means is incapable of specifying a blinking cycle at a value less than the order of milliseconds. Therefore, it is effective to apply the temporal coding method of the present invention to such display means.

The number of OFF periods to be changed to an ON period is monotonously increased or decreased. For example, a temporal coding condition of 1/7, 2/7, 3/7, 4/7, 5/7 and 6/7 is performed in order of 1/7, 2/7, 3/7, 4/7, 5/7 and 6/7, or in order of 6/7, 5/7, 4/7, 3/7, 2/7, and 1/7, with time.

Further, in the above example, the temporal coding was performed using the frequency that was determined by the smaller specified cycle (for example, 16 ms), among the two frequencies to be interpolated; however, it is also possible to use the frequency that is determined by the greater specified cycle (for example, 18 ms). For example, it is possible to cause blinking by way of the intermediate display method shown in the first row of Table 1 by using a specified cycle of 18 ms (ON period=9 ms).

As in the aforementioned example, this method also records information corresponding to the flicker threshold at the time that the test subject operates the operation unit of the mobile phone.

The features of the present invention are more specifically described below in reference to Examples.

Example 1

Figure 5:
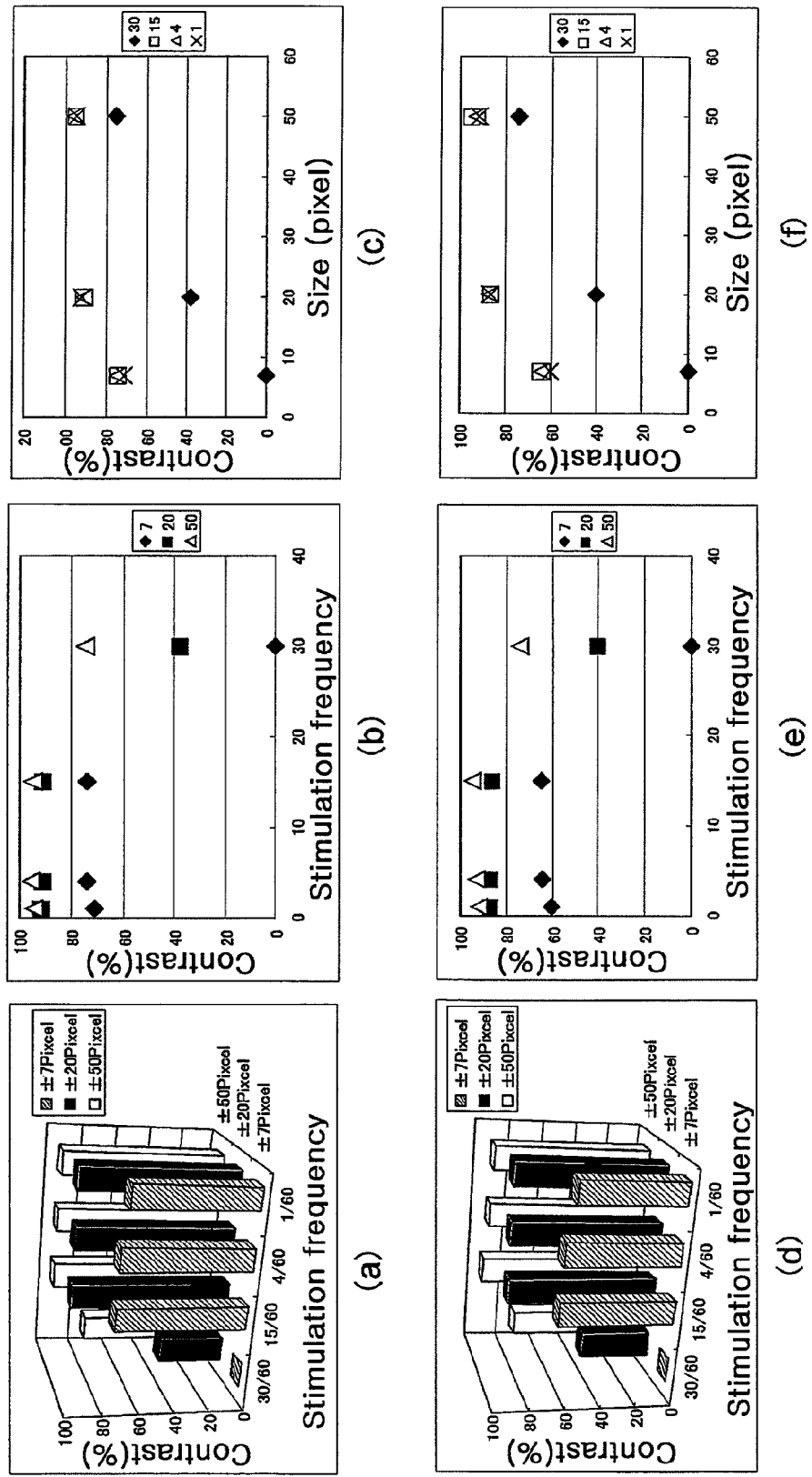
[FIG. 5] Graphs showing examples of test results.

An experiment was performed by changing the stimulation frequency (corresponding to the temporal coding condition), contrast, and size of a stimulation target (image) displayed on a liquid crystal screen refreshed at 60 Hz, so as to determine the time at which the test subject perceived flicker. The stimulation frequency was changed in four stages: 1/60, 4/60, 15/60, and 30/60. The size of the circle used as the stimulation target (the pattern shown in FIG. 4) was changed in three stages: ±7 pixels (viewing angle=0.4°), ±20 pixels (viewing angle=1.1°), and ±50 pixels (viewing angle=2.9°). Under these 4×3=12 conditions, the ON/OFF contrast of the stimulation target was changed by decreasing the OFF condition (luminance in OFF state) by 0.5% per second from 100:100, so as to find a contrast value at which the test subject started perceiving flicker. FIG. 5 shows the results of three measurements per condition, performed by two test subjects.

In FIG. 5, the stimulation frequency n/60 (n=1, 4, 15, 30) indicates the number (n) of OFF cycles per second. Further, the size of the stimulation target is expressed by the number of pixels starting with the pixel that resides in the center of the image, as one pixel, and counting linearly to the pixel in the outermost circumference.

Figure 6:
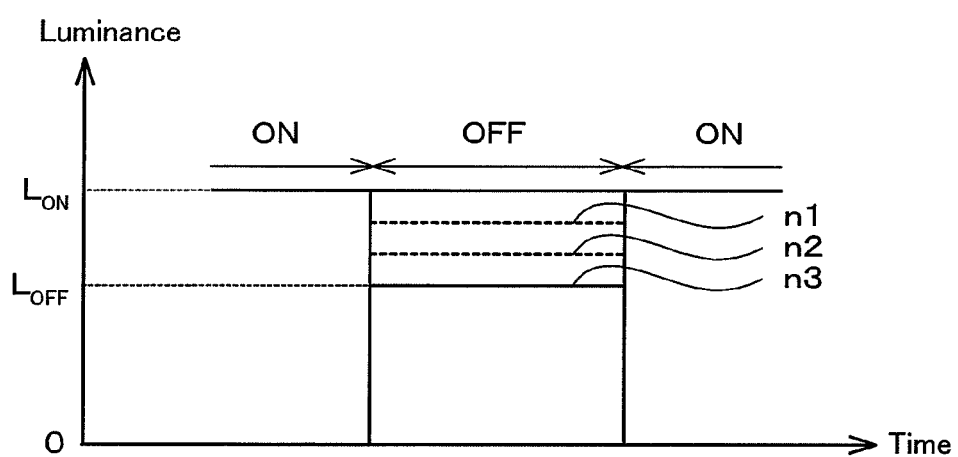
[FIG. 6] A drawing showing changes in contrast.

As shown in FIG. 6, "contrast" refers to a ratio (%) of the luminance value of an OFF pixel ($L_{OFF}$) to the luminance value of an ON pixel ($L_{ON}$), found by $100 L_{OFF}/L_{ON}$. Accordingly, as shown in FIG. 6, a decrease in contrast indicates setting the luminance value of the ON pixels to a constant value ($L_{ON}$) and decreasing the luminance value of the OFF pixels ($L_{OFF}$) by 0.5% of $L_{ON}$ per second (the decrease rate is constant) from the value of $L_{ON}$ to 0, which is shown as n1, n2 and n3 in FIG. 6. Since the ON pixels have a constant luminance value $I_{ON}$, decreasing the luminance value of the OFF pixels is equivalent to decreasing the contrast.

FIGS. 5(a) to 5(c), and FIGS. 5(d) to 5(f) show the results of Test Subjects A and B, respectively. The data of FIG. 5 reveals the following.

1: As the stimulation frequency (ON/OFF frequency per second) increased, a decrease in the contrast (100 $L_{OFF}/L_{ON}$ (%)) of the OFF reaction at which the test subject started perceiving flicker, in other words, an increase in the contrast ratio ($L_{ON}/L_{OFF}$) at which the test subject started perceiving flicker, was observed for three stimulation target sizes. More specifically, for both Test Subjects A and B, as shown in FIGS. 5(b) and (e), the contrast was clearly decreased at the stimulation frequency of 30/60 compared to those at the stimulation frequencies of 15/60, 4/60, and 1/60. Accordingly, as the stimulation frequency increased, flicker became less visible.

2: As the size of the stimulation target increased, an increase in the contrast of the OFF reaction at which the test subject started perceiving flicker, in other words, a decrease in the contrast ratio at which the test subject started perceiving flicker, was observed. More specifically, as shown in FIGS. 5(c) and 5(f), the contrast decreased in both cases of Test Subjects A and B with a decrease in the size of the stimulation target from ±50 pixels, ±20 pixels, to ±7 pixels. Accordingly, as the size of the stimulation target increased, flicker became more visible.

Therefore, by measuring the contrast at which the test subject starts perceiving flicker, it becomes possible to evaluate the fatigue level. The following explains the difference between the present invention (the method of changing contrast), and the conventional measurement method.

Figure 7:
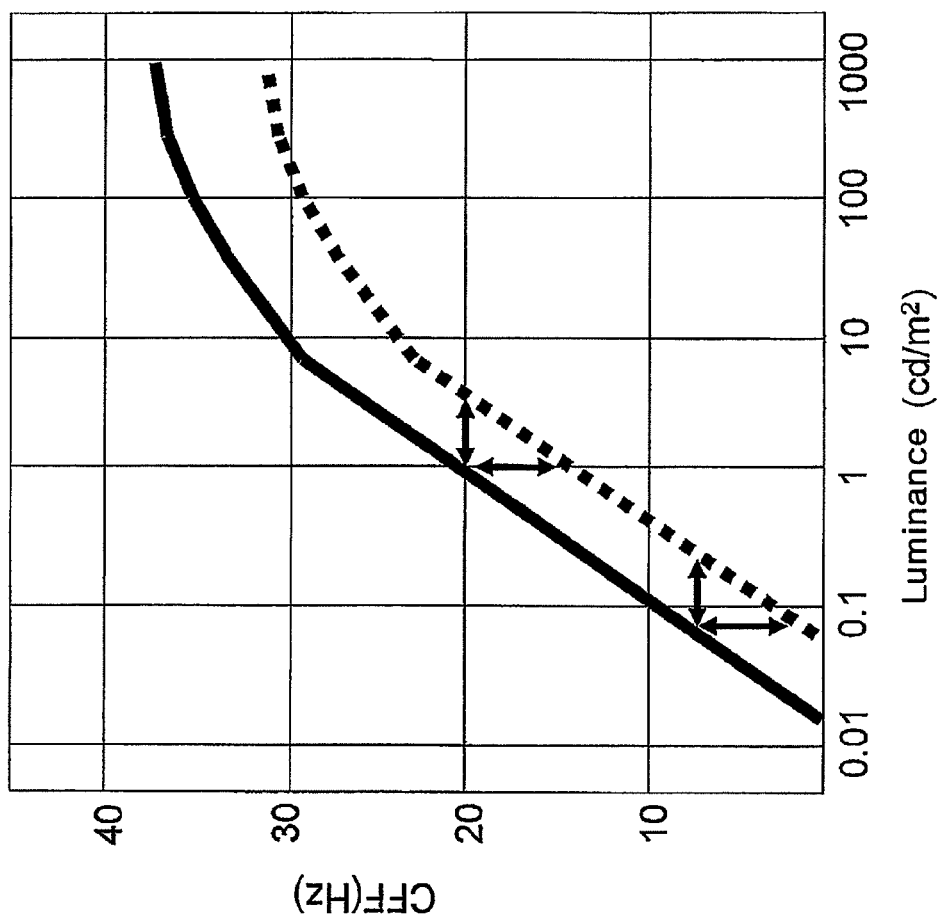
[FIG. 7] A graph conceptually showing differences between the present invention and a conventional method.

FIG. 7 is a graph showing how the relationship between the luminance of the image presented to the test subject and the flicker value changes according to the fatigue of the test subject. The horizontal axis denotes the luminance (cd/m$^2$) of the image presented to the test subject, and the vertical axis denotes the flicker value CFF (Hz). The solid curved line denotes the measurement result when the test subject is free from fatigue, and the broken curved line denotes the measurement result when the test subject is experiencing fatigue. As shown in the figure, it is known that the measurement result of the flicker value CFF changes depending on the fatigue of the test subject, as shown in the change from the solid curved line to the broken curved line (for example, see Railway Labour Science 4; 65-72, 1953, "Shihyo oyobi haikei no akarusa to miekata (vision and brightness of target and background)" Kunie Hashimoto et al.). In the conventional method, the flicker value CFF at a specific luminance is measured, and the fatigue level is evaluated by finding the change from the flicker value CFF obtained when the test subject was free from fatigue. Therefore, in the conventional method, the fatigue level is evaluated according to the degree of change from the solid curved line to the broken curved line in the vertical axis direction. In contrast, the inventors of the present invention switched the concept to conceive of evaluating the fatigue level by finding the degree of change from the solid curved line to the broken curved line in the horizontal axis direction.

Example 2

Figure 8:
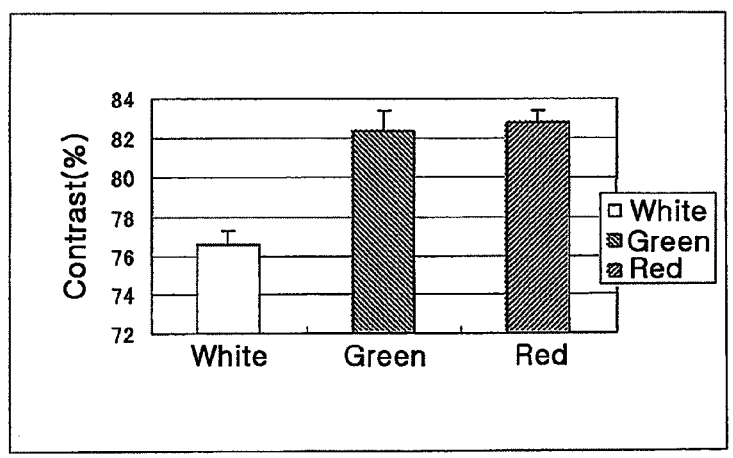
[FIG. 8] Graphs showing examples of other test results.
Figure 8:
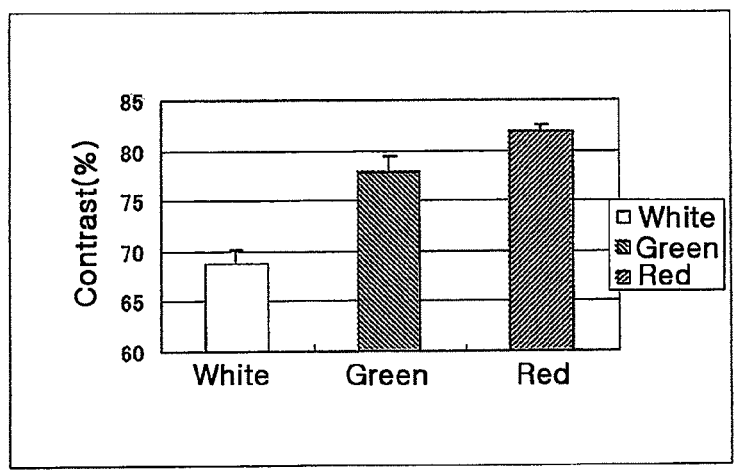

Using a liquid crystal screen refreshed at 60 Hz, the contrast at which the test subject started perceiving flicker was found by changing the color of the stimulation target to white, green, and red. The stimulation frequency was set to $^{10}$⁄₆₀, the size of the stimulation target was set to ±15 pixels (viewing angle 0.9°), and the OFF contrast for the ON and OFF of the stimulation was decreased by 1% in 2 seconds. FIG. 8 shows the results of five measurements per condition, performed by Test Subjects A and B.

When the color of the stimulation target was changed from white, to green, to red, in the above stimulation conditions, the decrease of the OFF contrast at which the test subject started perceiving flicker in the stimulation target was: white 76.6%, green=82.4%, and red=82.8% for Test Subject A; and white=68.8%, green=77.8%, and red=81.8% for Test Subject B. This revealed that flicker became more easily seen by changing the color to white, green, and red.

Example 3

To evaluate the reliability of the present invention, the results were compared with the measurement results of a conventional flicker measurement device. The contrast of the stimulation was changed using the temporal-spatial coding method of the present invention, and the manner in which the flicker threshold (corresponding to the flicker value) changed in accordance with the fatigue load was examined. Specifically, the test subjects were given a fatigue load of all-night labor from daytime to the next morning, and the flicker thresholds were measured while changing the contrast of the stimulation (image) using a personal computer (hereinafter referred to as a PC) and a mobile phone. Similarly, using the LED of a Windows (registered trademark) mobile device (hereinafter referred to as a mobile device) and a standard flicker device (a commercially available flicker value measurement device), the flicker thresholds (these denote the flicker value) were measured while changing the frequency of the displayed stimulation.

The measurement test is more specifically explained below. Two healthy adults were chosen as test subjects (Test Subjects A and B). On the previous day, the test subjects had sufficient sleep and rest, so they participated in the test with no fatigue. The flicker values were measured in the above-described four ways, first at 2:30 pm, and every two hours thereafter. Between the measurements, each test subject had a predetermined work task, and was allowed to take meals as required. The final measurement was performed at 8:30 am on the next day. Thereafter, each test subject had a short sleep before being subjected to another flicker value measurement in the above-described four ways. In the measurements, the standard flicker device, the PC, the mobile phone, and the mobile device were used in this order, and five measurements were performed with each device.

The details of the displayed stimulation are as follows. A MacBook Pro (Apple) was used as the PC. On its monitor, a white circular image (stimulation) 4 mm in diameter was displayed on a black background. The contrast of the stimulation was changed at a ratio of 0.5% per second in terms of the percentages of 256 steps of gradation. More specifically, assuming that the maximum value of the stimulation (luminance) was expressed as 100%, and the stimulation was linearly changed in 256 steps of gradation in a range between 0 to 100%, each step is 0.39% (=100/255). Therefore, changing the stimulation of a given value at a ratio of 0.5% can be performed by determining the step of gradation closest to the target stimulation (%) resulting from the 0.5% change. The stimulation was displayed at a speed of 30 times per second.

A Docomo SH906i (manufactured by Sharp Corporation) was used as the mobile phone. The stimulation was displayed in the same manner as in the PC, except that the contrast of the stimulation was expressed by 256 steps of gradation and was changed at a speed of 1 step per second. The stimulation was displayed at a speed of 15 times per second.

A Willcom WSO11SH (manufactured by Sharp Corporation) was used as the mobile device. Of the three 1-mm square LEDs on the upper left side of the display, the rightmost green LED related to the power supply was blinked. The blinking state of the LED was maintained for 1 second, then the LED was turned OFF for 0.5 second, and this sequence was repeated. Determining this sequence of ON and OFF as 1 cycle (1.5 seconds), the LED frequency was decreased from 60 Hz at a rate of 0.5 Hz per cycle.

A Roken Digital Flicker Model RDF-1 (manufactured by Shibata Co., Ltd.) was used as the standard flicker device. A red stimulation target was displayed while decreasing the frequency from 55 Hz at a rate of 1 Hz per second.

Figure 9:
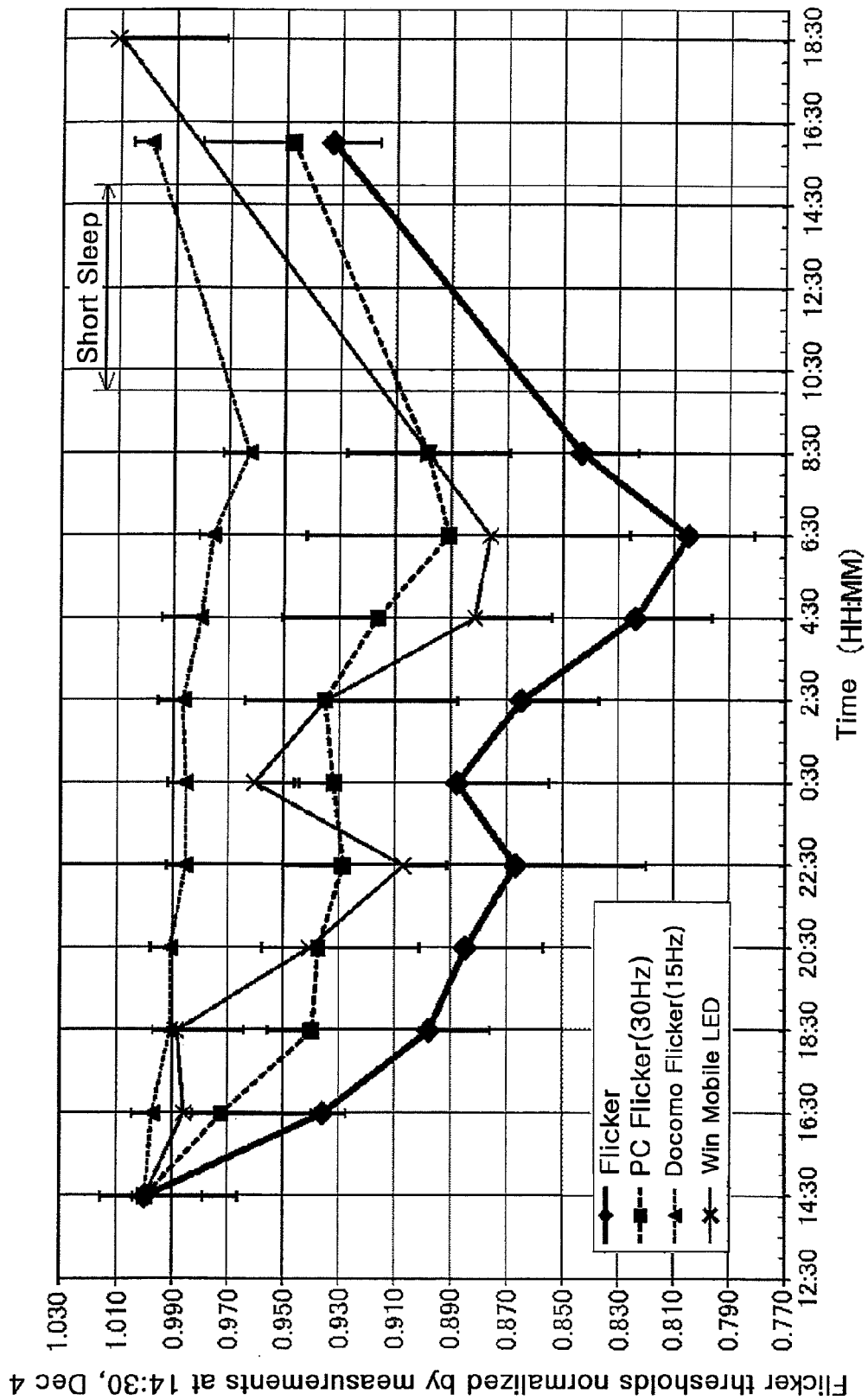
[FIG. 9] A graph showing results of a flicker threshold measurement for Test Subject A.
Figure 10:
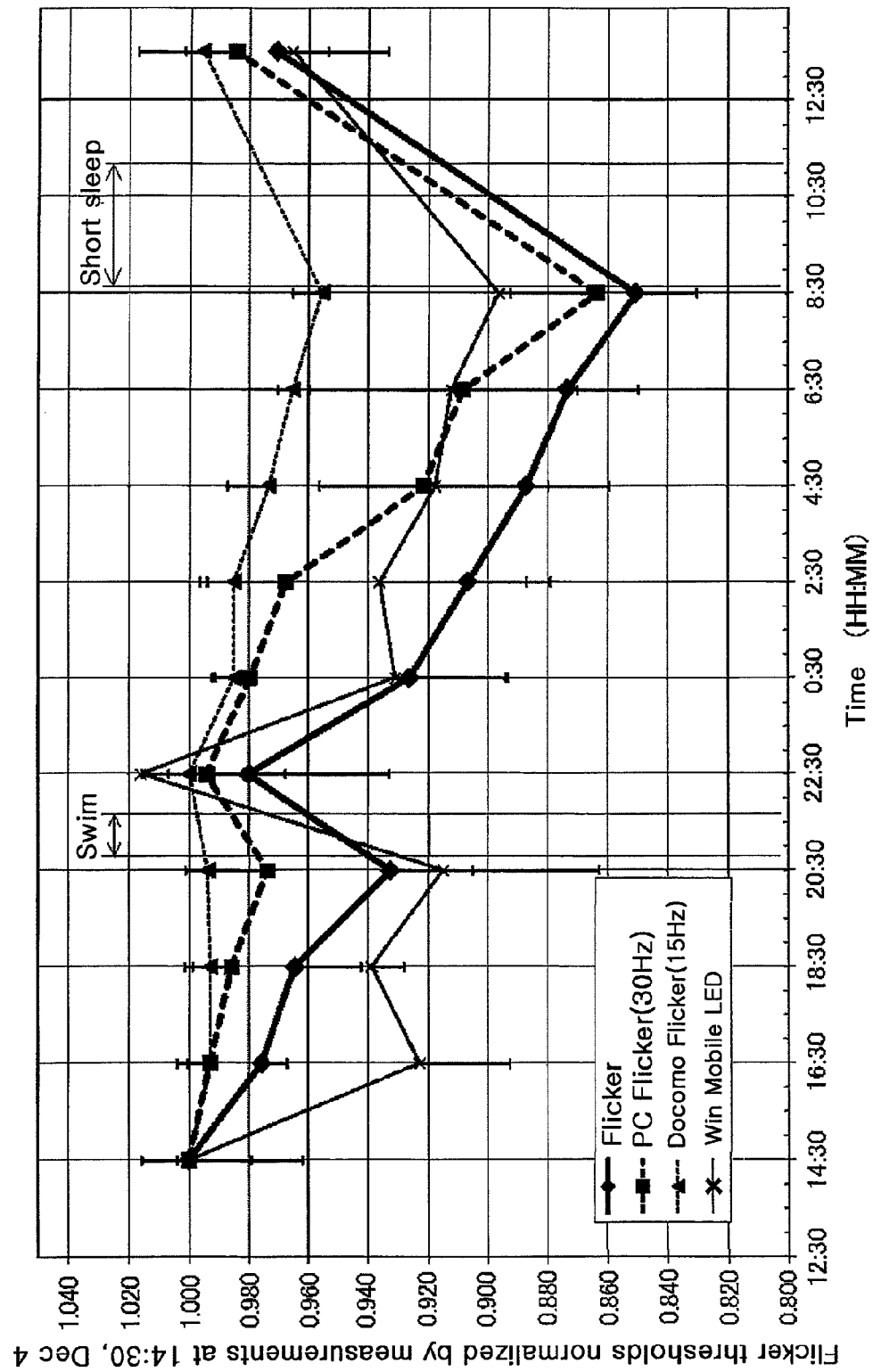
[FIG. 10] A graph showing results of a flicker threshold measurement for Test Subject B.

FIGS. 9 and 10 show graphs of the measurement results of Test Subjects A and B, respectively. In these figures, the vertical axis denotes the flicker thresholds normalized by the measurement values at 2:30 pm. More specifically, the measurement values at 2:30 pm are set to 1, and the values obtained thereafter are plotted proportional to 1.

These figures reveal that the flicker thresholds measured in the above four ways gradually decreased with time in the cases of both Test Subjects A and B. Then, the flicker thresholds became lowest at the 6:30 am or 8:30 am measurements on the next day. The figures also reveal that, after each test subject had a short sleep, all of the flicker thresholds measured in the four ways recovered to substantially the same levels as those measured at 4:30 pm and 6:30 pm on the previous day. Further, when the values measured in the four ways are normalized with their variation widths, respectively, in other words, when the maximum value and the minimum value are plotted within same width, the flicker thresholds show substantially the same tendency. Accordingly, the changes in measurement values obtained by the standard flicker device were substantially duplicated in the measurement values obtained by all of the above devices, i.e., PC, mobile phone, and mobile device.

As described, it was confirmed that the flicker thresholds measured in the four ways were decreased by a fatigue load caused by all-night labor, and that the fatigue was recovered by taking a short sleep break. It was also shown that the flicker thresholds measured according to the method of the present invention reflect the fatigue conditions, as with the flicker values measured by the conventional method.

INDUSTRIAL APPLICABILITY

The present invention is able to evaluate the fatigue of a test subject by using a computer or a mobile phone, which are now both widely used, in the same manner as in the conventional standard flicker value measurement method. Moreover, the simple measurement and evaluation of the present invention are useful for the health-care management of a test subject.

| [Reference Numerals] | |
| --- | --- |
| 1 | Arithmetic processing unit (CPU) |
| 2 | Read-only memory (ROM) |
| 3 | Rewritable memory (RAM) |
| 4 | Recording unit |
| 5 | Clock unit |
| 6 | Interface unit (IF unit) |
| 7 | Internal bus |
| 8 | Display unit |
| 9 | Operation unit |
| 10 | Test subject |

The invention claimed is:

1. A flicker threshold measurement device, comprising:
an arithmetic processing unit;
a display unit that refreshes an image at a specific refresh rate; and
an operation unit,
wherein:
the arithmetic processing unit sets a duration of each of ON periods and OFF periods according to a number of consecutive units of time with one refresh time being defined as one ON period and a consecutive OFF period, and increases or decreases the number of consecutive units of time to determine a duration of consecutive ON and OFF periods, such that the arithmetic processing unit displays the image on the display unit in an ON/OFF manner at a specific timing;
the arithmetic processing unit changes a timing of the specific timing by monotonously increasing or decreasing a number of ON periods, during which the image is displayed, per second, and a number of OFF periods, during which the image is not displayed, per second;
each of the ON periods and each of the OFF periods is a reciprocal of the refresh rate;
the arithmetic processing unit determines the number of ON periods and the number of OFF periods per second at a time when a test subject operates the operation unit as the test subject starts or stops perceiving flicker, as information corresponding to a flicker threshold; and
the arithmetic processing unit fixes or changes a ratio of a number of sets of an ON period and a consecutive OFF period comprised of a certain number of units of time to a number of sets of an ON period and a consecutive OFF period comprised of an increased or decreased number of units of time to determine the specific timing.

2. The flicker threshold measurement device according to claim 1, wherein the arithmetic processing unit monotonously increases or decreases with time at least one of a number of OFF pixels in the image, a size of the image, and a contrast of the OFF pixels, during a period in which the specific timing is not changed.

3. The flicker threshold measurement device according to claim 2, wherein the arithmetic processing unit changes a color of the image with time, during a period in which the specific timing is not changed.

4. The flicker threshold measurement device according to claim 1, wherein the arithmetic processing unit changes a color of the image with time, during a period in which the specific timing is not changed.

5. A flicker threshold measurement device, comprising:
an arithmetic processing unit;
a display unit that refreshes an image at a specific refresh rate; and
an operation unit,
wherein:
the arithmetic processing unit sets a duration of each of ON periods and OFF periods according to a number of consecutive units of time with one refresh time being defined as one ON period and a consecutive OFF period, and increases or decreases the number of consecutive units of time to determine a duration of consecutive ON and OFF periods, such that the arithmetic processing unit displays the image on the display unit in an ON/OFF manner at a specific timing;
the arithmetic processing unit monotonously increases or decreases at least one of a number of OFF pixels in the image, a size of the image, and a contrast of the OFF pixels, with time;
the arithmetic processing unit determines the number of OFF pixels, the size of the image, and the contrast of the OFF pixels at a time when a test subject operates the operation unit as the test subject starts or stops perceiving flicker, as information corresponding to a flicker threshold; and
the arithmetic processing unit fixes or changes a ratio of a number of sets of an ON period and a consecutive OFF period comprised of a certain number of units of time to a number of sets of an ON period and a consecutive OFF period comprised of an increased or decreased number of units of time to determine the specific timing.

6. The flicker threshold measurement device according to claim 5, wherein the arithmetic processing unit changes a color of the image with time, during a period in which the specific timing is not changed.

7. A flicker threshold measurement device, comprising:
an arithmetic processing unit;
a display unit that refreshes an image at a specific refresh rate; and
an operation unit,
wherein:
the arithmetic processing unit sets a duration of each of ON periods and OFF periods according to a number of consecutive units of time with one refresh time being defined as one ON period and a consecutive OFF period, and increases or decreases the number of consecutive units of time to determine a duration of consecutive ON and OFF periods, such that the arithmetic processing unit displays the image on the display unit in an ON/OFF manner at a specific timing;

the arithmetic processing unit changes a color of the image with time;

the arithmetic processing unit determines color information of the image at a time when a test subject operates the operation unit as the test subject starts or stops perceiving flicker, as information corresponding to a flicker threshold; and the arithmetic processing unit fixes or changes a ratio of a number of sets of an ON period and a consecutive OFF period comprised of a certain number of units of time to a number of sets of an ON period and a consecutive OFF period comprised of an increased or decreased number of units of time to determine the specific timing.

8. A process for measuring a flicker threshold using an apparatus comprising:

an operation unit; and a display unit that refreshes an image at a specific refresh rate, the process comprising the steps of:
1) displaying the image on the display unit in an ON/OFF manner at a specific timing according to a sub-step of setting a duration of each of ON periods and OFF periods according to a number of consecutive units of time with one refresh time being defined as one ON period and a consecutive OFF period, and a sub-step of increasing or decreasing the number of consecutive units of time to determine a duration of consecutive ON and OFF periods;
2) changing a timing of the specific timing by monotonously increasing or decreasing a number of ON periods, during which the image is displayed, per second, and a number of OFF periods, during which the image is not displayed, per second; and
3) determining the number of ON periods and the number of OFF periods per second at a time when a test subject operates the operation unit as the test subject starts or stops perceiving flicker, as information corresponding to a flicker threshold, wherein:
each of the ON periods and each of the OFF periods is a reciprocal of the refresh rate; and
the specific timing is determined by fixing or changing a ratio of a number of sets of an ON period and a consecutive OFF period comprised of a certain number of units of time to a number of sets of an ON period and a consecutive OFF period comprised of an increased or decreased number of units of time.

9. The process according to claim 8, further comprising the step of:
4) monotonously increasing or decreasing with time at least one of a number of OFF pixels in the image, a size of the image, and a contrast of the OFF pixels, during a period in which the specific timing is not changed.

10. The process according to claim 9, further comprising the step of
5) changing a color of the image with time, during a period in which the specific timing is not changed.

11. The process according to claim 8, further comprising the step of:
5) changing a color of the image with time, during a period in which the specific timing is not changed.

12. A process for measuring a flicker threshold using an apparatus comprising:

an operation unit; and a display unit that refreshes an image at a specific refresh rate, the process comprising the steps of:
1) displaying the image on the display unit in an ON/OFF manner at a specific timing according to a sub-step of setting a duration of each of ON periods and OFF periods according to a number of consecutive units of time with one refresh time being defined as one ON period and a consecutive OFF period, and a sub-step of increasing or decreasing the number of consecutive units of time to determine a duration of consecutive ON and OFF periods;
2) monotonously increasing or decreasing at least one of a number of OFF pixels in the image, a size of the image, and a contrast of the OFF pixels, with time; and
3) determining the number of OFF pixels, the size of the image and the contrast of the OFF pixels at a time when a test subject operates the operation unit as the test subject starts or stops perceiving flicker, as information corresponding to a flicker threshold, wherein the specific timing is determined by fixing or changing a ratio of a number of sets of an ON period and a consecutive OFF period comprised of a certain number of units of time to a number of sets of an ON period and a consecutive OFF period comprised of an increased or decreased number of units of time.

13. The process according to claim 12, further comprising the step of
5) changing a color of the image with time, during a period in which the specific timing is not changed.

14. A process for measuring a flicker threshold using an apparatus comprising:

an operation unit; and a display unit that refreshes an image at a specific refresh rate, the process comprising the steps of:
1) displaying the image on the display unit in an ON/OFF manner at a specific timing according to a sub-step of setting a duration of each of ON periods and OFF periods according to a number of consecutive units of time with one refresh time being defined as one ON period and a consecutive OFF period, and a sub-step of increasing or decreasing the number of consecutive units of time to determine a duration of consecutive ON and OFF periods;
2) changing a color of the image with time; and
3) determining color information of the image at a time when a test subject operates the operation unit as the test subject starts or stops perceiving flicker, as information corresponding to a flicker threshold, wherein the specific timing is determined by fixing or changing a ratio of a number of sets of an ON period and a consecutive OFF period comprised of a certain number of units of time to a number of sets of an ON period and a consecutive OFF period comprised of an increased or decreased number of units of time.

15. A flicker threshold measurement device, comprising:

an arithmetic processing unit;

a blinking unit capable of being turned ON and OFF at a changeable blinking frequency; and an operation unit, wherein:
the arithmetic processing unit specifies a first blinking cycle and a second blinking cycle of the blinking unit in units of milliseconds;

the arithmetic processing unit turns ON and OFF the blinking unit by monotonously increasing or decreasing with time a number of sets of an ON period and a consecutive OFF period, wherein each of ON periods and OFF periods is increased or decreased, so as to be changed by a unit of time in milliseconds among n consecutive sets of ON and OFF periods, where n is a number of third frequencies that can be set between a first frequency corresponding to the first blinking cycle and a second frequency corresponding to the second blinking cycle;

a duration of an OFF period is half of a duration of the first blinking cycle or half of a duration of the second blinking cycle; and the arithmetic processing unit determines a number of sets of consecutive ON and OFF periods, wherein each of the ON periods and the OFF periods is increased or decreased, so as to be changed by the unit of time among the consecutive sets of the ON and OFF periods when a test subject operates the operation unit as the test subject starts or stops perceiving flicker, as information corresponding to a flicker threshold.

16. A process for measuring a flicker threshold using an apparatus comprising:
an operation unit; and
a blinking unit capable of being turned ON and OFF at a changeable blinking frequency,
the process comprising the steps of:
1) specifying a first blinking cycle and a second blinking cycle of the blinking unit in units of milliseconds;
2) turning ON and OFF the blinking unit by monotonously increasing or decreasing with time a number sets of an ON period and a consecutive OFF period, wherein each of ON periods and OFF periods is increased or decreased, so as to be changed by a unit of time in milliseconds among n consecutive sets of ON and OFF periods, where n is a number of third frequencies that can be set between a first frequency corresponding to the first blinking cycle and a second frequency corresponding to the second blinking cycle; and
3) determining a number of sets of consecutive ON and OFF periods, wherein each of the ON periods and the OFF periods is increased or decreased, so as to be changed by the unit of time among the consecutive sets of the ON and OFF periods when a test subject operates the operation unit as the test subject starts or stops perceiving flicker, as information corresponding to a flicker threshold,
wherein a duration of the OFF period is half of a duration of the first blinking cycle or half of a duration of the second blinking cycle.

17. A non-transitory computer-readable storage medium having stored thereon a program for flicker threshold measurement using an apparatus comprising an operation unit and a display unit that refreshes an image at a specific refresh rate, the program enabling the apparatus to implement:
a first function of displaying the image on the display unit in an ON/OFF manner at a specific timing according to a sub-step of setting a duration of each of ON periods and OFF periods according to a number of consecutive units of time with one refresh time being defined as one ON period and a consecutive OFF period, and a sub-step of increasing or decreasing the number of consecutive units of time to determine a duration of consecutive ON and OFF periods;

a second function of changing a timing of the specific timing by monotonously increasing or decreasing a number of ON periods, during which the image is displayed, per second, and a number of OFF periods, during which the image is not displayed, per second; and
a third function of determining the number of ON periods and the number of OFF periods per second at a time when a test subject operates the operation unit as the test subject starts or stops perceiving flicker, as information corresponding to a flicker threshold,
wherein:
each of the ON periods and each of the OFF periods is a reciprocal of the refresh rate; and
the specific timing is determined by fixing or changing a ratio of a number of sets of an ON period and a consecutive OFF period comprised of a certain number of units of time to a number of sets of an ON period and a consecutive OFF period comprised of an increased or decreased number of units of time.

18. The non-transitory computer-readable storage medium having stored thereon a program for flicker threshold measurement according to claim 17, the program further causing the apparatus to implement a fourth function of monotonously increasing or decreasing with time at least one of a number of OFF pixels in the image, a size of the image, and a contrast of the OFF pixels, during a period in which the specific timing is not changed.

19. The non-transitory computer-readable storage medium having stored thereon a program for flicker threshold measurement according to claim 17, the program further causing the apparatus to implement a fifth function of changing a color of the image with time, during a period in which the specific timing is not changed.

20. A non-transitory computer-readable storage medium having stored thereon a program for flicker threshold measurement using an apparatus comprising an operation unit and a display unit that refreshes an image at a specific refresh rate, the program causing the apparatus to implement:
a first function of displaying the image on the display unit in an ON/OFF manner at a specific timing according to a sub-step of setting a duration of each of ON periods and OFF periods according to a number of consecutive units of time with one refresh time being defined as one ON period and a consecutive OFF period, and a sub-step of increasing or decreasing the number of consecutive units of time to determine a duration of consecutive ON and OFF periods;
a second function of increasing or decreasing at least one of a number of OFF pixels in the image, a size of the image, and a contrast of the OFF pixels, with time; and
a third function of determining the number of OFF pixels, the size of the image and a contrast of the OFF pixels at a time when a test subject operates the operation unit as the test subject starts or stops perceiving flicker, as information corresponding to a flicker threshold,
wherein the specific timing is determined by fixing or changing a ratio of a number of sets of an ON period and a consecutive OFF period comprised of a certain number of units of time to a number of sets of an ON period and a consecutive OFF period comprised of an increased or decreased number of units of time.

21. The non-transitory computer-readable storage medium having stored thereon a program for flicker threshold measurement according to claim 20, the program further allowing the apparatus to implement a fifth function of changing a color of the image with time, during a period in which the specific timing is not changed.

22. A non-transitory computer-readable storage medium having stored thereon a program for flicker threshold measurement using an apparatus comprising an operation unit and a display unit that refreshes an image at a specific refresh rate, the program causing the apparatus to implement:
- a first function of displaying the image on the display unit in an ON/OFF manner at a specific timing according to a sub-step of setting a duration of each of ON periods and OFF periods according to a number of consecutive units of time with one refresh time being defined as one ON period and a consecutive OFF period, and a sub-step of increasing or decreasing the number of consecutive units of time to determine a duration of consecutive ON and OFF periods;
- a second function of changing a color of the image with time; and
- a third function of determining color information of the image at a time when a test subject operates the operation unit as the test subject starts or stops perceiving flicker, as information corresponding to a flicker threshold,
- wherein the specific timing is determined by fixing or changing a ratio of a number of sets of an ON period and a consecutive OFF period comprised of a certain number of units of time to a number of sets of an ON period and a consecutive OFF period comprised of an increased or decreased number of units of time.

23. The non-transitory computer-readable storage medium having stored thereon a program for flicker threshold measurement according to claim 22, the program further causing the apparatus to implement a fifth function of changing a color of the image with time, during a period in which the specific timing is not changed.

24. A non-transitory computer-readable storage medium having stored thereon a program for flicker threshold measurement using an apparatus comprising an operation unit and a display unit that refreshes an image at a specific refresh rate, the program causing the apparatus to implement:
- a first function of specifying a first blinking cycle and a second blinking cycle of the blinking unit in units of milliseconds;
- a second function of turning ON and OFF the blinking unit by monotonously increasing or decreasing with time a number sets of an ON period and a consecutive OFF period, wherein each of ON periods and OFF periods is increased or decreased, so as to be changed by a unit of time in milliseconds among n consecutive sets of ON and OFF periods, where n is a number of third frequencies that can be set between a first frequency corresponding to the first blinking cycle and a second frequency corresponding to the second blinking cycle; and
- a third function of determining a number of sets of consecutive ON and OFF periods, wherein each of the ON periods and the OFF periods is increased or decreased, so as to be changed by the unit of time among the consecutive sets of the ON and OFF periods when a test subject operates the operation unit as the test subject starts or stops perceiving flicker, as information corresponding to a flicker threshold,
- wherein a duration of the OFF period is half of a duration of the first blinking cycle or half of a duration of the second blinking cycle.

* * * * *